US011504060B2

(12) United States Patent
Keels

(10) Patent No.: US 11,504,060 B2
(45) Date of Patent: Nov. 22, 2022

(54) DENTAL RETAINER WITH PH SENSOR

(71) Applicant: Martha Ann Keels, Chapel Hill, NC (US)

(72) Inventor: Martha Ann Keels, Chapel Hill, NC (US)

(73) Assignee: Martha Ann Keels, Chapel Hill, NC (US)

( * ) Notice: Subject to any disclaimer, the term of this patent is extended or adjusted under 35 U.S.C. 154(b) by 61 days.

(21) Appl. No.: 15/631,074

(22) Filed: Jun. 23, 2017

(65) Prior Publication Data

US 2018/0368766 A1    Dec. 27, 2018

(51) Int. Cl.
*A61B 5/00*    (2006.01)
*A61B 5/145*   (2006.01)

(52) U.S. Cl.
CPC .......... *A61B 5/682* (2013.01); *A61B 5/14539* (2013.01); *A61B 5/4211* (2013.01); *A61B 5/002* (2013.01); *A61B 5/14507* (2013.01)

(58) Field of Classification Search
CPC ... A61B 5/14539; A61B 5/4211; A61B 5/682; A61B 5/0002; A61B 5/0015; A61B 5/002; A61B 5/0024; A61B 5/14507; A61B 5/1468; A61B 5/1477; A61B 5/4547; A61B 5/0004; A61B 5/4842; A61B 2562/04
See application file for complete search history.

(56) References Cited

U.S. PATENT DOCUMENTS

| | | | |
|---|---|---|---|
| 4,629,424 A * | 12/1986 | Lauks | A61B 5/0002 257/417 |
| 5,604,817 A * | 2/1997 | Massen | A61C 9/006 382/120 |
| 6,258,046 B1 * | 7/2001 | Kimball | A61B 5/0084 600/504 |
| 6,604,528 B1 | 8/2003 | Duncan | |
| 7,661,955 B2 * | 2/2010 | Da Cruz | A61C 7/10 433/7 |
| 8,813,753 B2 | 8/2014 | Bhat et al. | |
| 9,492,115 B2 | 11/2016 | Stein et al. | |
| 2004/0133089 A1 * | 7/2004 | Kilcoyne | A61B 5/4233 600/350 |
| 2007/0106138 A1 * | 5/2007 | Beiski | A61B 10/0051 600/349 |
| 2008/0004547 A1 | 1/2008 | Dinsmoor et al. | |

(Continued)

FOREIGN PATENT DOCUMENTS

WO    2005115225 A2    12/2005

OTHER PUBLICATIONS

Ganesh, M., Hertzberg, A., Nurko, S., Needleman, H., & Rosen, R. (2016). Acid rather than non-acid reflux burden is a predictor of tooth erosion. Journal of pediatric gastroenterology and nutrition, 62(2), 309. (Year: 2016).*

(Continued)

*Primary Examiner* — Eric F Winakur
*Assistant Examiner* — Alice Ling Zou
(74) *Attorney, Agent, or Firm* — Meunier Carlin & Curfman LLC

(57) ABSTRACT

An oral insert includes at least one pH sensor in electronic communication with a power source and a data transceiver. The pH sensor is exposed to fluids in the patient's mouth and measures the pH of the fluids to determine fluid composition.

15 Claims, 13 Drawing Sheets

(56) References Cited

U.S. PATENT DOCUMENTS

| | | | |
|---|---|---|---|
| 2008/0234599 A1* | 9/2008 | Chiao | A61B 5/4233 600/547 |
| 2009/0149722 A1* | 6/2009 | Abolfathi | G16H 10/65 600/301 |
| 2011/0028803 A1* | 2/2011 | Ollmar | A61B 5/14539 600/301 |
| 2011/0054938 A1* | 3/2011 | Hood | A61B 5/00 705/3 |
| 2011/0140703 A1* | 6/2011 | Chiao | C23C 28/345 324/438 |
| 2011/0184319 A1 | 7/2011 | Mack et al. | |
| 2012/0220986 A1* | 8/2012 | Wolff | A61M 31/002 604/892.1 |
| 2014/0134561 A1 | 5/2014 | Smith et al. | |
| 2014/0248574 A1* | 9/2014 | Yoon | A61C 7/14 433/199.1 |
| 2015/0216641 A1* | 8/2015 | Popa-Simil | A61B 5/7405 433/8 |
| 2015/0305671 A1* | 10/2015 | Yoon | A61B 5/681 600/301 |
| 2015/0374274 A1* | 12/2015 | Jovanovski | A61B 5/682 600/309 |
| 2016/0066776 A1 | 3/2016 | Weiss et al. | |
| 2016/0338626 A1* | 11/2016 | Wang | A61B 5/682 |
| 2017/0080249 A1* | 3/2017 | Brawn | A61N 5/0625 |
| 2017/0087363 A1* | 3/2017 | Costanzo | G16H 20/10 |
| 2017/0252140 A1* | 9/2017 | Murphy | A61C 7/10 |
| 2017/0290545 A1* | 10/2017 | Zerick | A61B 5/7405 |

OTHER PUBLICATIONS

Nagashima, et al., "Measurement of Skin Surface pH with a Non-invasive Dry pH Sensorm", 2015 5th International Conference on Biomedical Engineering and Technology (ICBET 2015), 5 pages.

Huang, "A pH Sensor Based on a Flexible Substrate", Presented to the Faculty of the Graduate School of The University of Texas at Arlington in Partial Fulfillment, 2010, 119 pages.

Kim, et al., "A Solid-State Thin-Film Ag/AgCl Reference Electrode Coated with Graphene Oxide and Its Use in a pH Sensor", Sensors 2015, 15, 6469-6482.

Mahbub, et al., "Electronic Sensor Interfaces With Wireless Telemetry", Advances in Bioengineering 2015, 151-175.

Tabata, et al., "Miniaturized Ir/IrOx pH Sensor for Quantitative Diagnostic of Dental Caries", Procedia Engineering 168, 2016, 598-601.

* cited by examiner

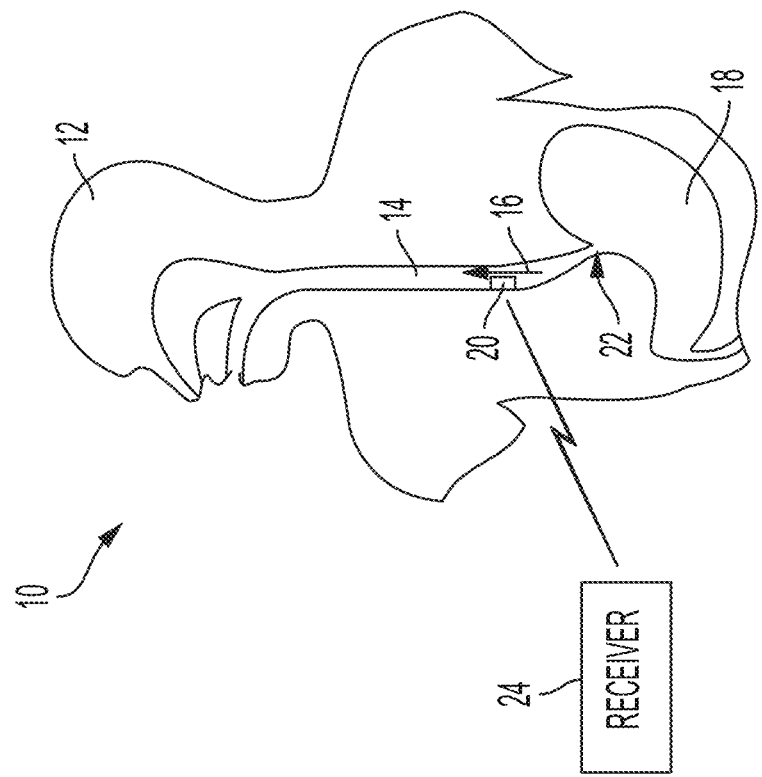
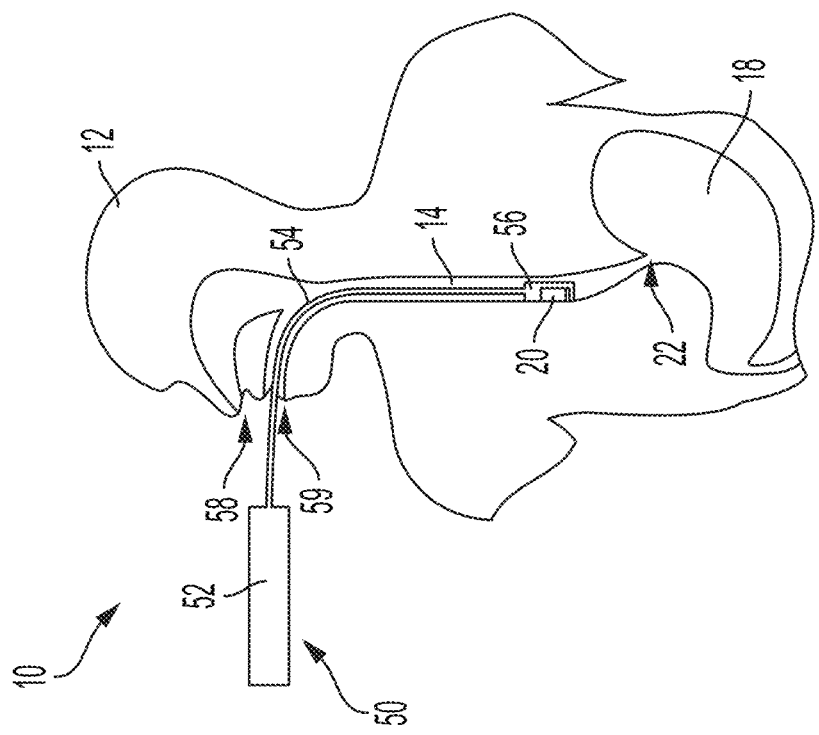

DENTAL RETAINER WITH PH SENSOR

FIELD OF THE INVENTION

This disclosure applies to the field of oral sensors for tracking, diagnosing, and treating acid erosion to a patient's teeth and oral cavity due to gastroesophageal reflux disease, acidic food intake, and similar conditions that cause a change in pH of fluids in a patient's mouth.

BACKGROUND

The mouths of humans and other animals include countless sources of biomarkers that are useful in medicine. Oral health can be used as a diagnostic tool, a resource for disease prevention, and an avenue for corrective action in regard to disease states. One of the conditions that can be tied to oral health is acid reflux disease. Not only can stomach acids cause problems with oral health, particularly in regard to dental acid erosion, but the oral cavity can be a considerably powerful tool in diagnosing both the presence of acid reflux disease and the dental effects of acid reflux disease. This is particularly true in patients who cannot always accurately convey their symptoms to a care provider for proper diagnosis. Even relatively healthy individuals may be experiencing acid reflux disease without realizing that the condition is present right away by conditioning themselves to ignore the symptoms or by experiencing symptoms when sleeping. Other patients are effected by dental acid erosion due to habitually consuming highly acidic food and drink. Patients who consistently sip acidic drinks all day, for example, are susceptible to dental acid erosion and other oral health risks without being aware of the changes in the pH of their mouth. New diagnostic tools are needed to characterize oral health for a patient in real time, during various normal activities, and in a passive manner that does not intrude on a patient's comfort or daily routine, including sleeping.

The prior art references shown in the attached figures include numerous embodiments of sensors used in the fields of gastroenterology, neurology, and dentistry, and some of the earlier work includes references to anatomical pH analyses. One of the most prevalent pH monitoring devices is shown in FIG. 1A as an esophageal implant that is temporarily attached to a patient's esophagus with a delivery and implant tool (50, 250) also shown in FIG. 2. The esophageal sensor (20) is illustrated in FIG. 1B attached to the wall of the esophagus (14) in a temporary connection that allows the sensor (20) to collect data regarding the internal environment of the esophagus, including pH measurements for the gastric fluids present in the patient's esophagus. After a predetermined period of data collection and transmission to an outside receiver (24), the sensor (20) is passed through the body. The wireless transmission of data from the esophageal sensor (20) to the receiver (24) is accomplished with a sensor arrangement of FIG. 2 including a transmitter (225), a battery (250), and a well (270) having the pH sensor capability.

FIGS. 1A and 1B illustrate a prior art system of installing an esophageal sensor (20) to the interior of the esophagus (14) by directing an installation extension (54) through the patient's oral cavity (59) and into the esophagus (14). The goal is to use the sensor to track the pH readings of fluids in the esophagus, particularly any acid reflux (16) from the patient's stomach (18) back into the esophagus via the lower esophageal sphincter (22). After a period of use, the sensor (14) naturally and automatically sloughs off with the mucosal lining of the esophagus and passes through the body. Using this device requires the patient to undergo either general anesthesia or IV sedation for sensor placement.

Another embodiment of a device that utilizes a similar concept as that shown in FIG. 1A is the pH probe placed by passing a thin, elongated and tubular probe instrument through the patient's nasal passages (58) and into the esophagus (14). The probe is usually left in place for 24 hours and is physically or electronically connected to a monitor outside the body that reads acid levels in the esophagus.

In either the esophageal sensor of FIGS. 1 and 2 or the nasal pH probe described above, measuring the pH of the oral cavity is entirely bypassed. None of the prior art pH devices designed particularly to test for acid reflux can provide any data on the pH of the fluids in a patient's mouth, the effect of acid erosion on the teeth, gingiva, and other oral tissue, or be used to assist in overall oral hygiene, dental care, or diet modification.

Other sensors that are known in the art of oral data collection include a sensor for gathering various chemical and compositional analyses from inside a patient's mouth via a bite guard or mouth piece (301) attached to the external structure of the mouth piece shown in FIG. 3. Similarly, general sensor devices have been attached to a patient's mouth as dental implants or other tooth attachments such as the device of FIG. 4 at Ref. 410. FIG. 5 shows a prior art mouth guard having sensors attached to the internal structure of a mouth piece or bite guard with a wired connection for transmitting data to an external analysis and monitoring device. These intra-oral devices incorporate numerous kinds of data collection configurations but are not necessarily appropriate for accurate chemical composition analysis, particularly in regard to the pH of saliva.

One challenge that has been problematic for developing prior art pH sensors for oral use is that of producing a pH sensor that has an appropriate size, shape, and scale. For a pH sensor to measure acid and base levels in a patient's mouth, the pH sensor must have a sensor structure that is comfortably positioned in the patient's mouth, preferably on a temporary or removable basis. Research in the area of pH sensors illustrates that modern devices may be made with flat cross sections of thin film structures that are reactive to pH changes. FIG. 6 shows one early device that utilized thin film construction for a pH sensor that was useful for dry pH measurement of the skin, and this kind of technology has been used internally as well. FIG. 7 illustrates a similarly flat kind of pH measuring electrode that is on a flexible substrate, making the pH sensor more conducive to the curvature of a particular structure being tested.

Prior art devices shown in FIG. 8 illustrate that pH sensors having a substantially flat or layered composition (e.g., thin film structures) may also have the benefit of a scale measured in millimeters and produced with a footprint that is minimized for internal use. Power supply and power conservation are considerations that have had to be overcome in developing small footprint pH sensors that are substantially flat and configured for both data collection and data transmission. Early efforts to provide power to internally positioned gastro-esophageal devices included uses of RF power transmission and inductive circuitry to allow for both data transmission and chargeable power storage. FIGS. 9 and 10 illustrate the kinds of circuits that have been used in this regard.

As batteries and telecommunications processing hardware have become more suitable for internal use, both in terms of composition and scale, a need in the art has arisen to take advantage of both electro-chemical sensing methods and devices as well as wireless data transmission on a microscale in the art of pH measurement for diagnosing acid reflux disorders. As noted above, the saliva of a patient represents an untapped source of numerous data types in regard to detecting and treating gastroesophageal reflux disease (GERD) and its detrimental effect on a patient's dental health. A convenient and comfortably used device to measure pH of a patient's saliva could be instrumental in diagnosing and treating gastroesophageal reflux disease (GERD). As described in the embodiments below, a pH sensor worn in a patient's mouth and continuously monitoring pH of saliva could allow a caregiver many more options for acid reflux data analysis in regard to both the medical condition of acid reflux disease and the dental condition of dental acid erosion. One prior art device that may provide a platform for an oral pH measurement is a traditional Hawley retainer used in orthodontics. The Hawley retainer has proven to be a reliable oral insert and well tolerated by dental patients for over 90 years. As shown in FIG. 11, a prior art Hawley retainer incorporates a synthetic body that conforms to the shape of a patient's mouth, more specifically the front of the roof of the mouth. The Hawley retainer includes connectors (1110) that fit against the patient's teeth (1105) and gingiva to hold the retainer in a secure position until manually removed by the wearer.

The prior art discussed herein emphasizes the current need to establish pH measurement in a device and monitoring system that can be temporarily affixed inside a patient's mouth with the components necessary for accurate pH sampling of saliva. The same is discussed in regard to the embodiments displayed herein.

BRIEF SUMMARY OF THE DISCLOSURE

In one embodiment, an oral pH sensor includes an oral insert configured for placement in a patient's mouth in a position proximate the roof of the mouth. The oral insert includes at least one pH sensor in electronic communication with a power source and a data transceiver. The pH sensor is exposed to fluids in the patient's mouth and measures the pH of the fluids to determine fluid composition. The pH data is analyzed to diagnose the presence of gastric fluids mixed with saliva, wherein the gastric fluids have traveled from the esophagus into the mouth, indicating acid reflux into the mouth from the patient's stomach and/or esophagus. The pH data can also be correlated with dietary acid exposures and determine the true acid exposure to the dentition and oral structures. The data collected may also be beneficial in differentiating GERD acid exposures from dietary acid exposures in the mouth.

BRIEF SUMMARY OF THE FIGURES

FIG. 1A is a PRIOR ART schematic diagram of a biomedical device used to implant sensors in the esophagus of a subject.

FIG. 1B is a PRIOR ART schematic diagram of the sensor of FIG. 1A implanted in a patient's esophagus.

DETAILED DESCRIPTION

This disclosure incorporates an apparatus, a method, and a system of measuring pH of oral fluids, including saliva and/or gastric fluid and/or mixes thereof, present in the patient's mouth. The term "pH" is used herein according to its broadest commonly used meaning in science. The reference to pH is commonly applied on a numeric scale used to specify acidity or basicity of a solution. Most references place the numeric scale in a range of 0 to 14, with pure water being a neutral value of seven (7), acids being denoted less than seven (<7), and bases denoted greater than seven (>7). The pH of a body fluid can be used to diagnose medical and dental conditions, including but not limited to gastroesophageal reflux disease, dental acid erosion in the mouth, and similar conditions by which gastric fluids from the stomach move up the esophagus and into the patient's mouth. The acids in the gastric fluids cause numerous harmful effects on the esophagus, the mouth, on the teeth, and related tissue. The pH sensor placed in a patient's mouth is also useful to determine incidents in which dietary habits or food intake changes the pH in the patient's mouth. One goal, therefore, is to identify and track pH trends in the patient's mouth with an oral insert having a pH sensor and then using that information for diagnosing and treating underlying medical conditions, dental effects, and sources of acid erosion in the mouth.

As described herein, these acids can be detected by a pH sensor placed within a patient's body in a position that tracks the change of pH in a given body fluid, including but not limited to saliva in the mouth. The term "saliva" as used herein is given its broadest plain meaning with the understanding that any patient's mouth will include saliva and mixes of food, drink, saliva and gastric fluids in various proportions throughout the day and night. The term "saliva" as used herein is not limited to any particular chemical composition of solution but generally refers to the body fluid detectable in a patient's mouth at any given time. It is notable that the term "saliva" as used herein is a general term referring to and including general body fluids, food/drink, and other aqueous solutions in the mouth that have mixed with pure saliva emitted from salivary glands. Saliva pH falling into lower ranges (e.g., less than or equal to a pH of approximately six (6)) indicates an acidity that can be corrosive of the teeth, gingiva, and the mouth in general. Numerous studies exist that identify saliva mixture pH levels considered unhealthy, and this disclosure is not limited to any one pH level or range of pH levels. The overall apparatus, system, and method disclosed herein track pH in a way that the changes of saliva pH are monitored for health purposes, whether in a diagnostic or treatment setting.

Figure 2:
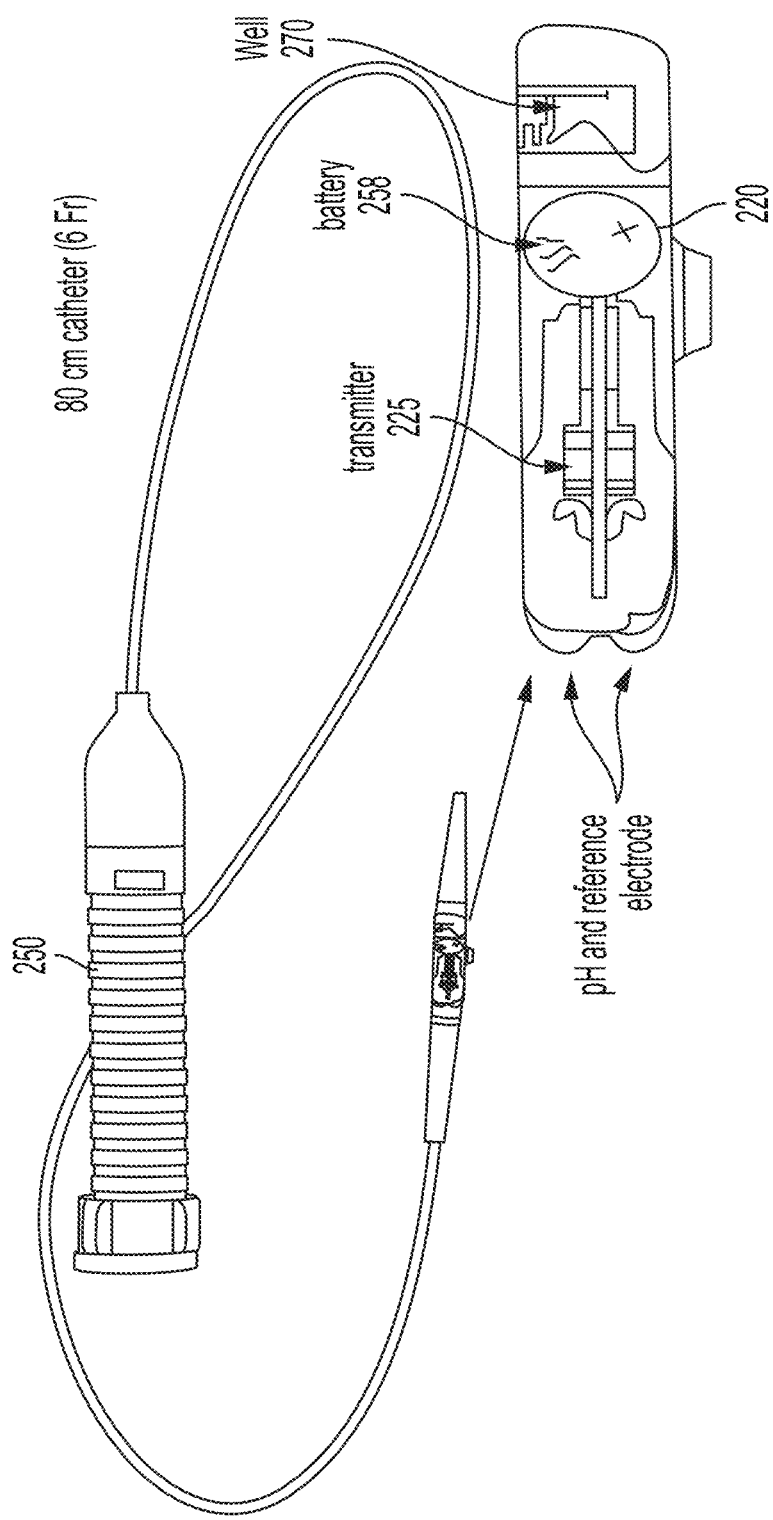
FIG. 2 is a PRIOR ART side perspective view of a wireless modular sensor as shown in FIGS. 1A and 1B.
Figure 3:
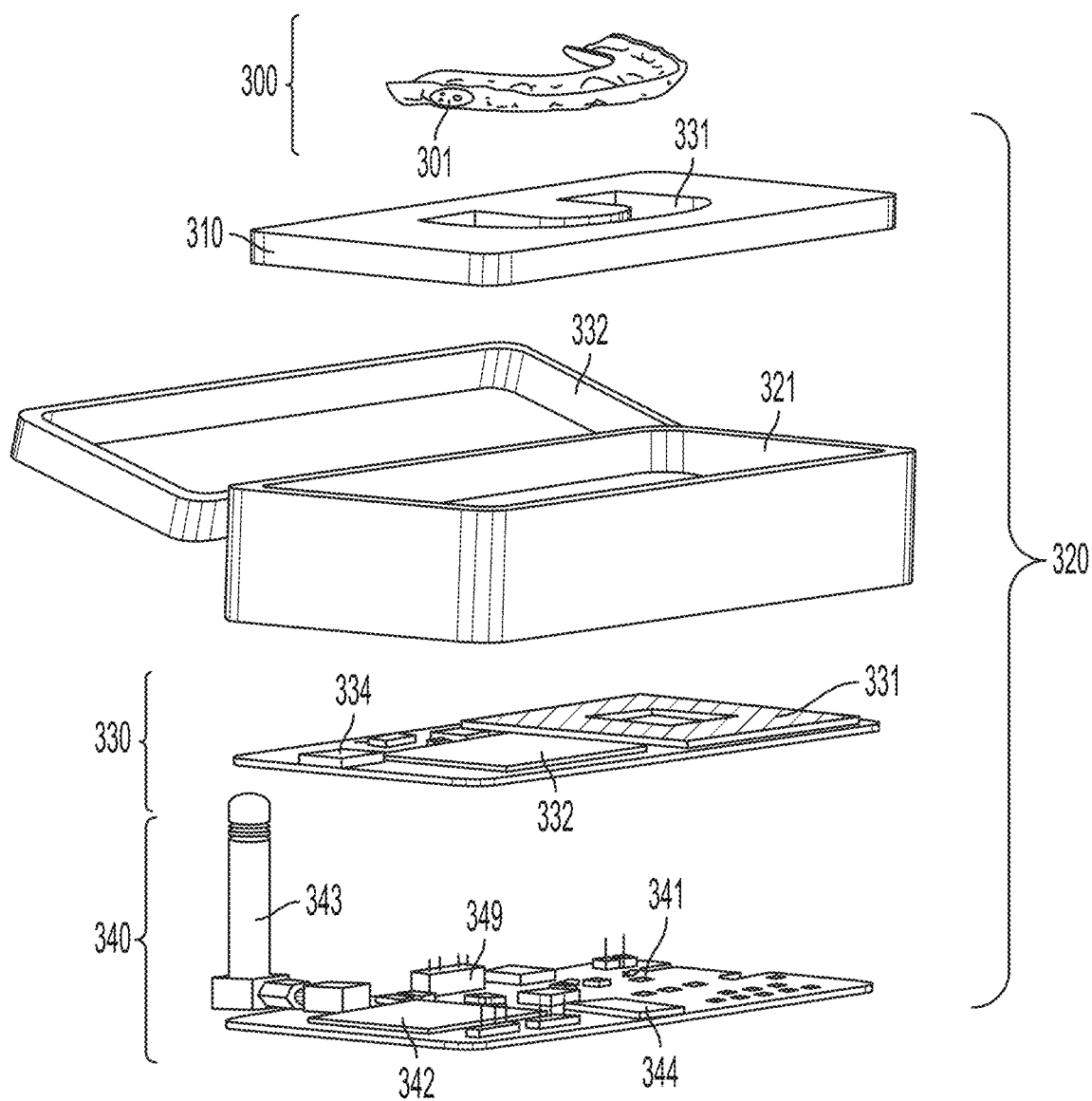
FIG. 3 is a PRIOR ART schematic diagram of a sensor system collecting data from a sensor placed on an exterior of a mouth piece insert.
Figure 4:
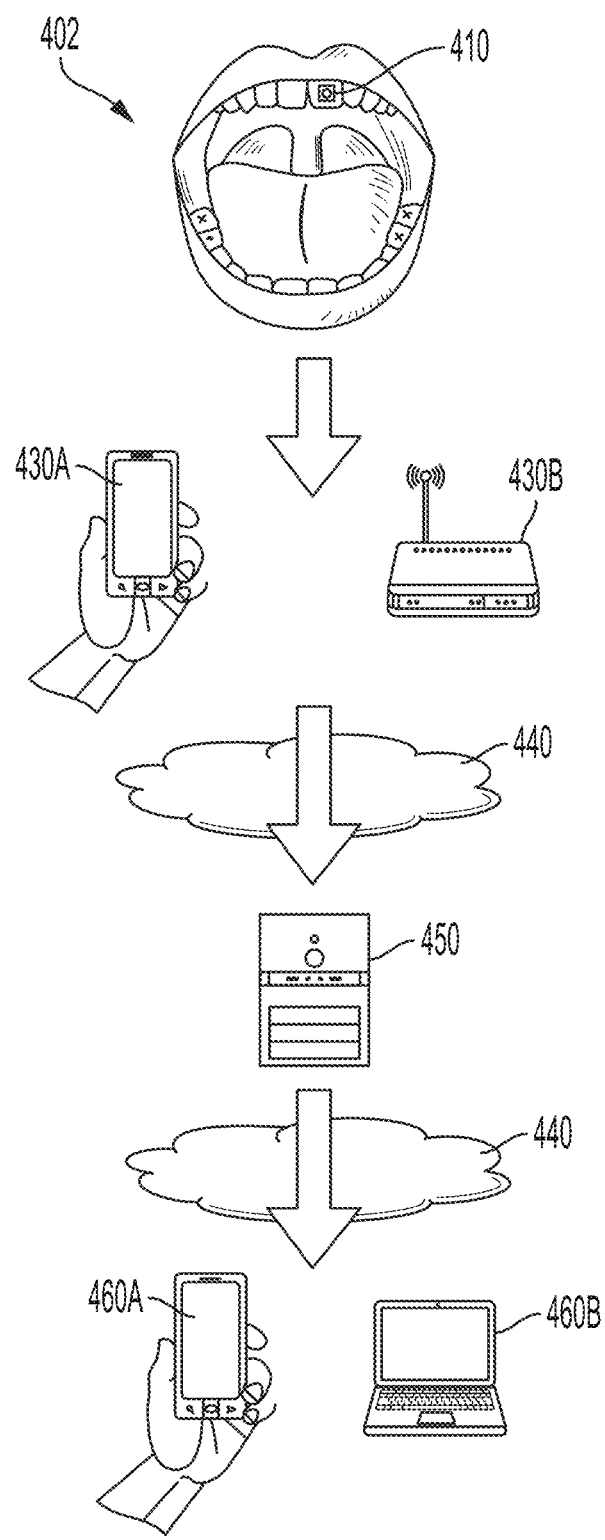
FIG. 4 is a PRIOR ART schematic diagram of a sensor system collecting data from a sensor placed on a dental device implanted within teeth of a patient.
Figure 5:
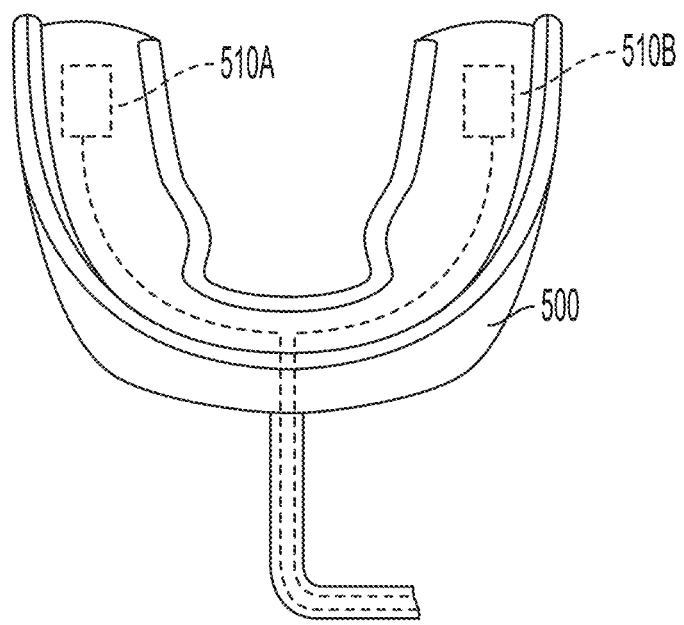
FIG. 5 is a PRIOR ART schematic diagram of a sensor system collecting data from a sensor placed on an interior of a mouth piece insert.
Figures 6A, 6B:
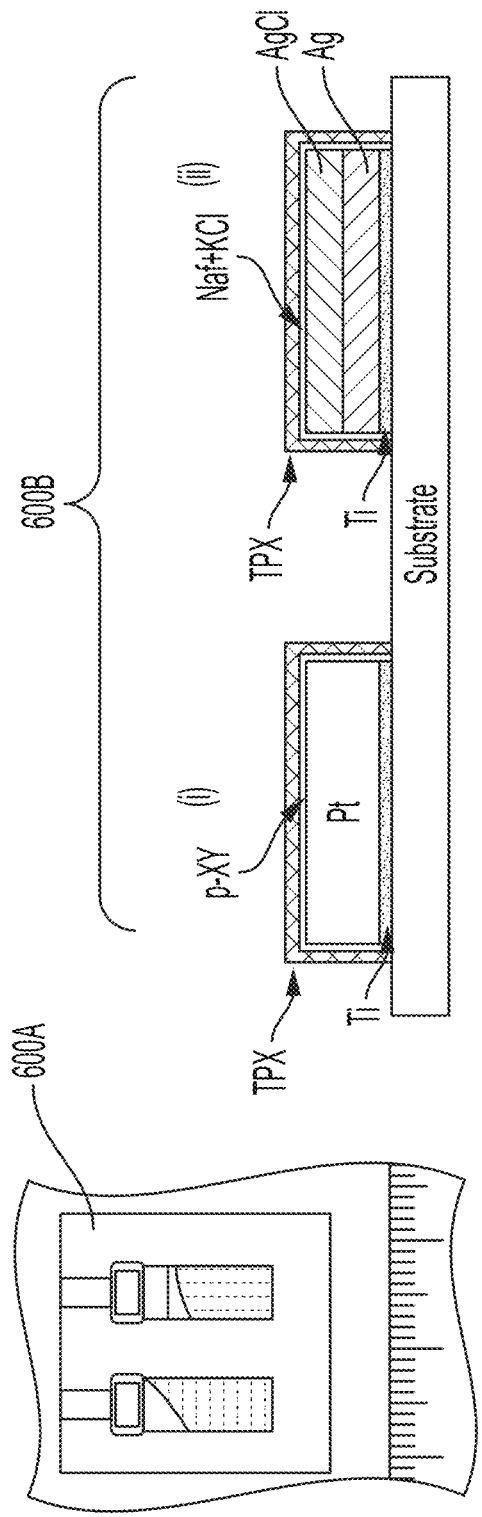
FIG. 6A is a top view of a PRIOR ART pH sensor formed as a series of flat layers.
FIG. 6B is a side cross sectional view of a PRIOR ART pH sensor of FIG. 6A.
Figure 7A:
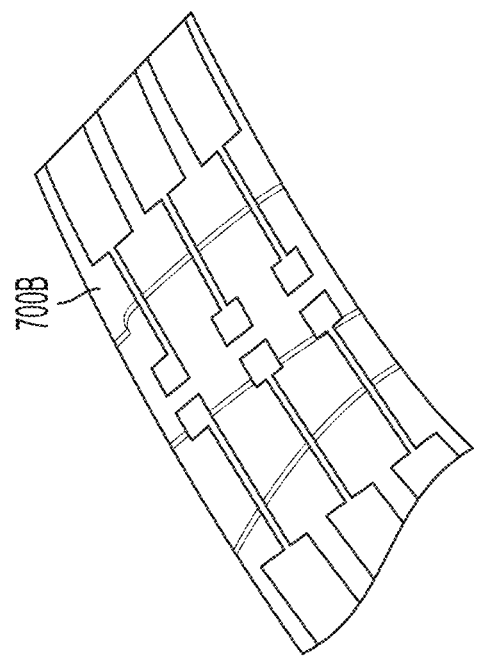
FIG. 7A is a side perspective view of a PRIOR ART pH sensor formed as a series of flat layers via electroplating techniques.
Figure 7B:
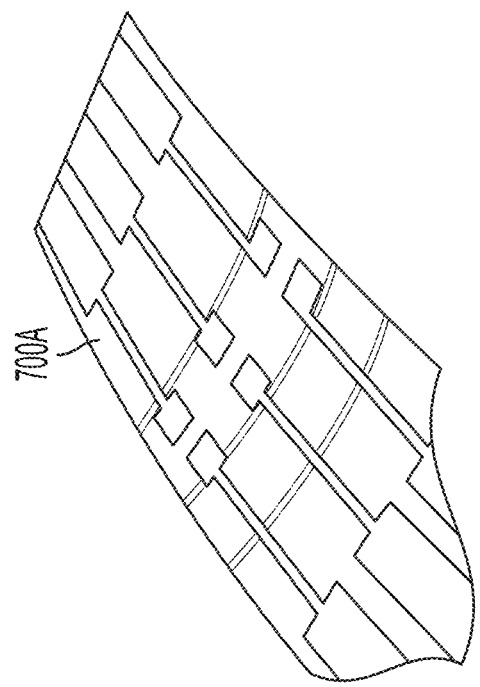
FIG. 7B is a side perspective view of the PRIOR ART pH sensor of FIG. 7A formed as a series of electroplated layers and subject to potassium chloride saturation processes.
Figure 8C:
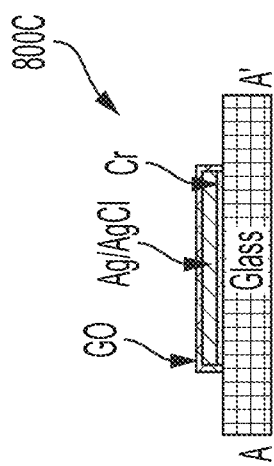
FIG. 8C is a side cross section view of the PRIOR ART pH sensor of FIG. 8B assembled as thin film layers.
Figure 8B:
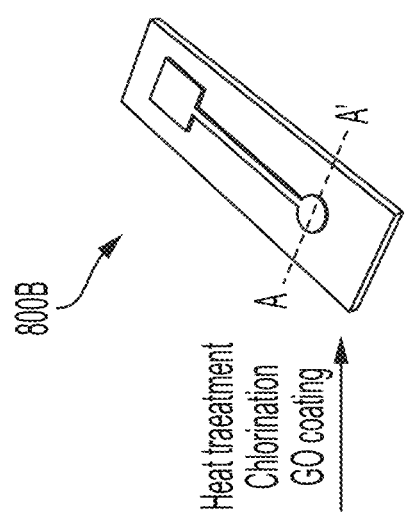
FIG. 8B is a top perspective view of the PRIOR ART pH sensor of FIG. 8A after further processing.
Figure 8A:
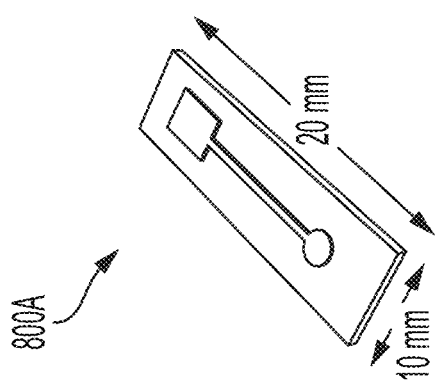
FIG. 8A is a top perspective view of a PRIOR ART pH sensor having a thin film construction in a substantially flat assembly.
Figure 9:
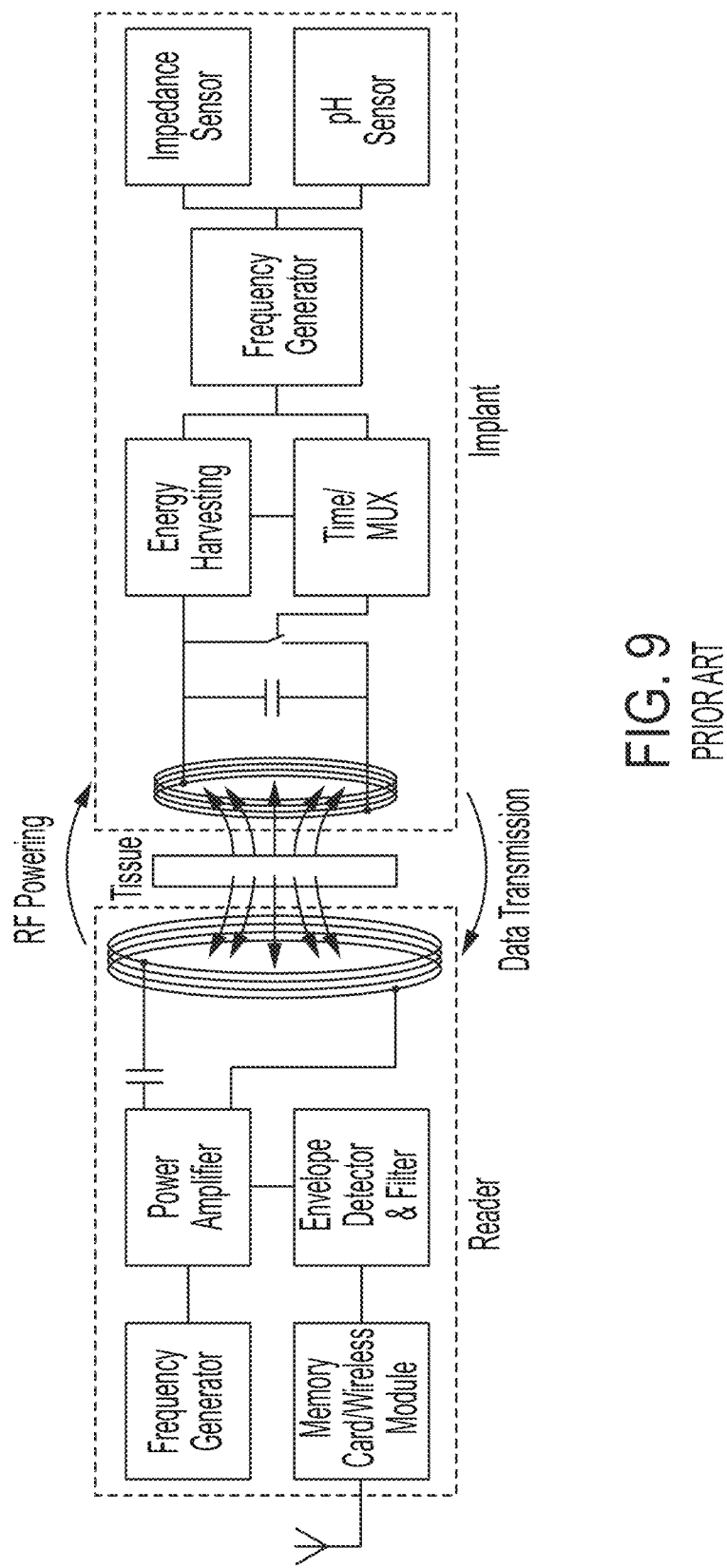
FIG. 9 is a PRIOR ART schematic of one kind of gastroesophageal reflux monitoring system.
Figure 10:
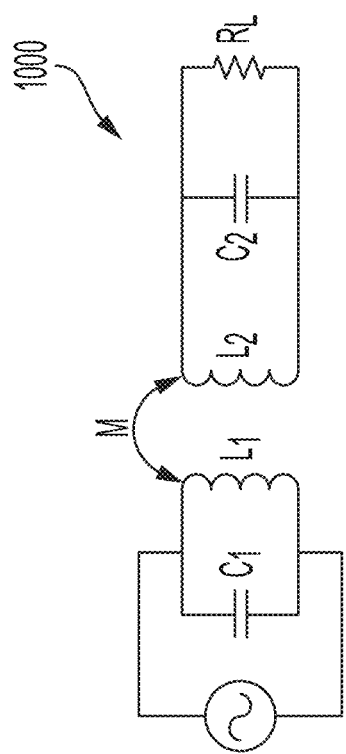
FIG. 10 is a PRIOR ART schematic of one kind of power circuit possible to use in implementing the monitoring system of FIG. 9 with power induced by inductive links.
Figure 11:
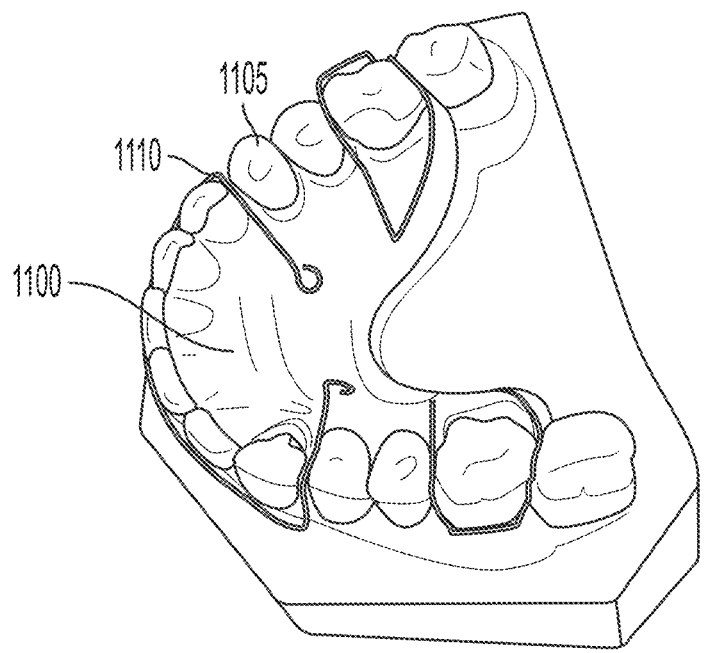
FIG. 11 is a top perspective view of a PRIOR ART Hawley retainer used for orthodontics and retaining alignment of orthodontic corrective procedures.

In one embodiment, an apparatus according to this disclosure includes an orally inserted device that may be referred to as a "retainer" or "mouth piece" or "mouth guard" in general terms to denote an overall shape. The oral device as used herein typically conforms to at least a portion of the shape of a patient's mouth. Without limiting the invention to any one embodiment, this disclosure includes oral inserts that conform to at least one of a roof of a patient's mouth, a patient's gingiva, a patient's teeth, or any location on which the oral inserts can temporarily affix during use. In one embodiment, the oral insert is manually inserted and removable by the patient similar to other known mouth guards. The oral insert preferably stays in place by fitting against at least a portion of the mouth, often the roof of the mouth, and may include Adams clasps and a labial bow that allow the patient's teeth to assist in holding the oral insert in place. As shown in the prior art FIG. 11, a standard Hawley retainer accommodates such a fit by being molded into a shape that conforms to the curvature and contours of a patient's palate, and teeth. The Hawley retainer of FIG. 11 is also shown with reinforced hardware (1110) in the shape of Adams clasps and a labial bow that engage the patient's teeth to hold the retainer more securely against the roof of the mouth. The Adams clasps (1110) and the labial bow (1112) provide a three prong retention system that fixes the Hawley retainer to the patient's mouth until manually removed. The prior art Hawley retainer (1100) is discussed herein only as an example of a kind of mouthpiece that may exhibit a shape and fit that accommodates other embodiments of this disclosure but is in no way limiting of the invention.

Figure 12:
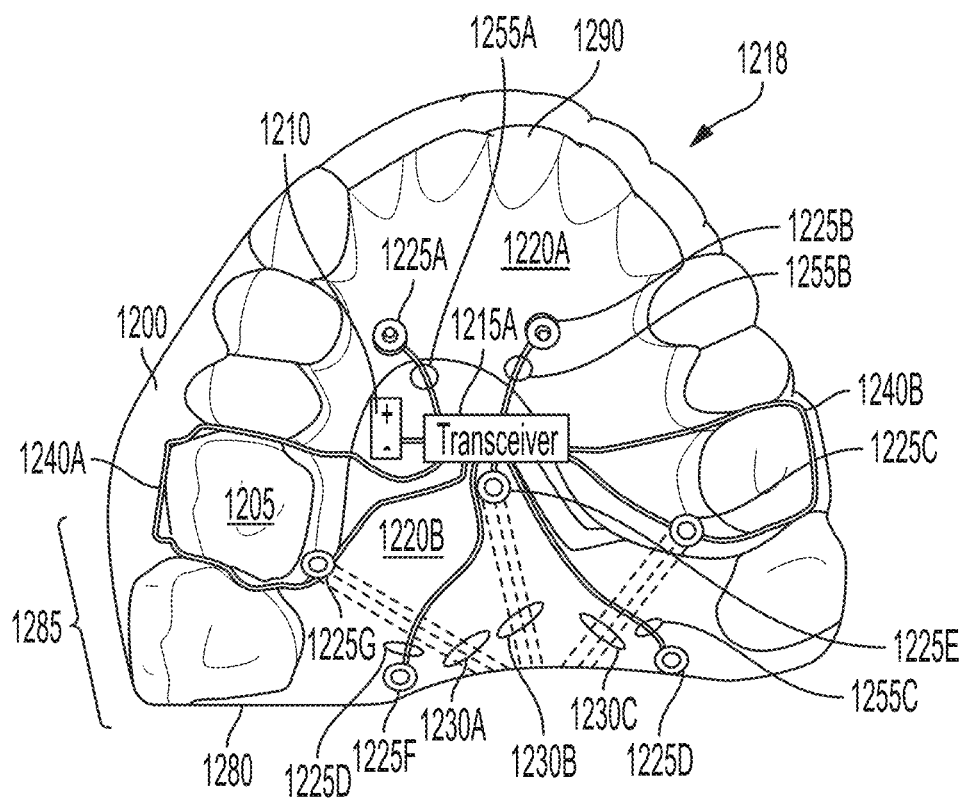
FIG. 12 is a top perspective view of an oral device such as a retainer having a pH sensor incorporated therein according to embodiments of this invention.

FIG. 12 is one example of a mouth piece, referred in some embodiments as an oral insert, that can be used to measure pH in a patient's mouth, particularly in regard to the pH of the patient's saliva. Again, one goal is to monitor pH of saliva (including mixtures of saliva, gastric fluids, food and drink) as present in the mouth at any given time, record pH readings over a sample period, and process those recordings with computerized data processing equipment for diagnostic and treatment purposes. The diagnostic and treatment purposes of the device shown in FIG. 12 may include, but are not limited to, detecting and monitoring acid reflux disease, dental acid erosion of the teeth, and sources of the acids including gastric acids as well as food and drink intake. The device may be helpful in confirming the fact that dental acid erosion has been and is occurring in a patient's mouth (even in instances when the patient is unaware) and further providing evidence of the source of that erosion, whether by acid reflux or dietary factors.

The device as shown in FIG. 12 may add value to many other areas of a patient's medical and dental care. For example, with saliva having a pH less than 5.0, permanent loss of enamel and tooth structure can result. The pH levels may increase a patient's susceptibility to oral cancers, and the pH monitor could be used in assisting with sleep apnea concerns. This disclosure is supplemented by the information of FIG. 13, which is a well-recognized set of standards used to evaluate, categorize, and document the severity of dental erosion due to dental acid erosion. This set of standards, referred to in the art as the Keels-Coffield Severity Scale, has been developed by the named inventor in this matter. The Keels-Coffield Severity Scale is particularly useful in diagnosing and treating gastroesophageal reflux disease (GERD) but is not limited to any one area.

Figure 13:
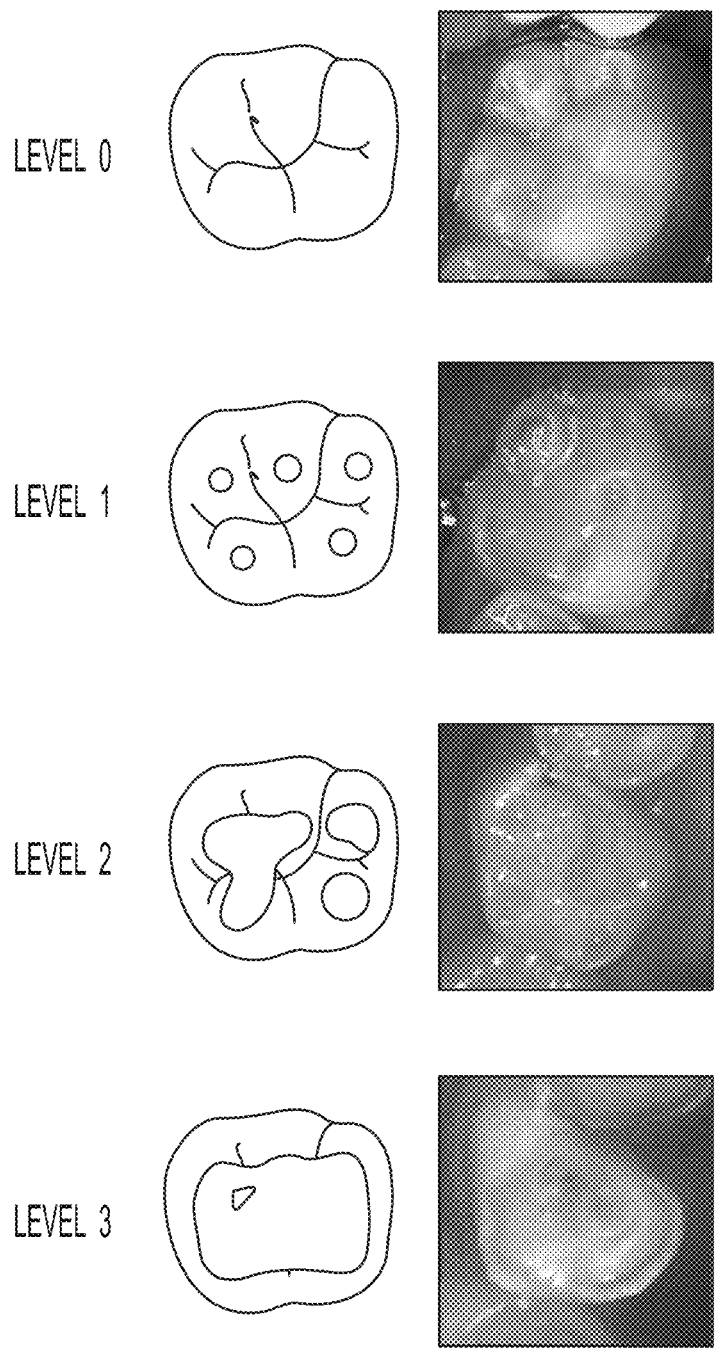
FIG. 13 is a schematic representation of the effects of dental acid erosion as numerous levels of tooth loss.

The chart summarizing the Keels-Coffield Severity Scale is attached as FIG. 13 and shows four levels of severity for dental acid erosion, respectively numbered as Level Zero (no erosion of the teeth present), Level 1 (mild erosion), Level Two (moderate erosion), and Level Three (severe erosion). Table 1 below summarizes the identification of severity at each level and certain possible treatment considerations for a hypothetical patient. The oral pH sensor disclosed herein could be used in conjunction with the Keels-Coffield Severity Scale to diagnose and treat gastroesophageal reflux disease, diet problems, and habitual triggers that eventually lead to severe dental acid erosion. None of these proposed uses of the system, device, and method of the present application should be considered limiting of the concepts of this disclosure in any way.

TABLE 1

Treatment Options as Determined by the Keels-Coffield Clinical Severity Scale of Dental Erosion.

| | |
|---|---|
| Level 0 NO EROSION | No Suggested Treatments |
| Level 1 MILD | If the child confirms a positive history of GERD symptoms, refer to his/her pediatrician or a GI specialist for testing and management. |
| | If there is no dental sensitivity, routine fluoride application and sealants may be adequate. |
| | If dental sensitivity occurs. protect the teeth with occlusal composite resin build-ups. |
| | Monitor and document the erosive lesions with photographs and/or casts (as tolerated by the child). |
| Level 2 MODERATE | Same recommendations as for MILD erosions, however, teeth with MODERATE erosions will require occlusal composite resin build-ups or SSC's to protect against further loss of tooth structure. |

TABLE 1-continued

Treatment Options as Determined by the Keels-Coffield Clinical Severity Scale of Dental Erosion.

| | |
|---|---|
| Level 3 SEVERE | Same recommendations for MILD and MODERATE erosions, however, teeth with SEVERE erosions may require pulp therapy or extraction (if non-restorable). |

An overall oral insert (1218) of FIG. 12 is one example of a device that may be temporarily positioned in the patient's mouth to measure pH of saliva therein. In FIG. 12, the oral insert (1218) may include a contoured region (1220A) that tracks the shape and fit of a patient's teeth and gingiva and a palate region that tracks the shape and fit of the roof of the patient's mouth. The contoured region (1220A) and the palate region (1220B) may be formed as one solitary piece via known processes such as but not limited to 3-D printing, molding and casting of plastics, polymers, resins, and the like. Numerous polymeric or even metal alloys are within the scope of this disclosure and no single material or method of manufacturing is limiting of the apparatuses, systems, or methods disclosed herein. In other embodiments, the contoured region and the palate region may be manufactured separately and even be made of different kinds of materials that are suitable for the relative positions and functions of the respective regions (1220A, 1220B) of the oral insert. In one non-limiting embodiment, the contoured region and the palate region may be permanently attached to each other, but in other circumstances, this disclosure encompasses a modular assembly allowing for the contoured region (1220A) and the palate region (1220B) to be separable at the option of the user and/or medical/dental provider. A separable arrangement of the contoured portion (1220A) and the palate portion (1220B) may be useful in manufacturing techniques, sensor placement, and for providing housings for other equipment placed within the mouth guard, or oral insert (1218), such as the battery (1210) and the transceiver (1215) shown in FIG. 12.

The oral insert (1218) depicted in FIG. 12 includes numerous sensors configured to sense and measure biomarkers in the mouth and saliva. In one embodiment, the sensors (1225A-1225G) are strategically placed and include at least one sensor (1225E, e.g.,) but typically a plurality of sensors (1225A-1225G) as shown in FIG. 12. In one embodiment, the sensor placement is determined according to the patient's anatomy, space availability on or within the oral insert, and/or a medical/dental provider's professional judgment regarding sensor positions likely to lead to the most accurate readings of a biomarker available in a given situation. For example, and without limiting this disclosure, in one embodiment, the sensors (1225A-1225G) include pH sensors that fit within the oral insert (1218) in preferred positions for measuring pH of a patient's saliva and transmitting the readings to a computerized component, such as but not limited to a transceiver (1215) that further transmits the pH data to a computer via a network as described below.

For embodiments in which the sensors are pH sensors (1225A-1225G), one embodiment allows for pH sensors to be scaled and constructed in a way that allows for comfortable placement in a patient's mouth (e.g., the flat, layered pH sensors discussed above could be one non-limiting option). At least one of these pH sensors is in contact with the patient's saliva during a sampling period to gather pH data about the saliva. The positions of the sensors (1225A-1225G) may be adjusted as necessary, and in one embodiment, the sensors may be placed on the mouth guard by the care provider after the mouth guard or oral insert has been manufactured. In this regard, the sensors may be attached to a previously manufactured oral insert device with adhesives that withstand the oral environment or even with mechanical fasteners (e.g., a pin mechanism attached to the back of the sensor that punctures the oral insert device and sticks the sensor into the body of the oral insert device). These kinds of arrangements allow for modular sensor placement by a medical/dental practitioner after considering the patient's anatomy and limitations of a mouth guard built for a particular patient.

In the example of FIG. 12, the oral insert device (1218) includes a proximal end (1280) relative to the patient's esophagus and a distal end (1290) relative to the patient's esophagus. The sensors (1225A-1225G) include pH sensors placed along the proximal end (1280) of the oral insert device (1218), as this position is closest to the sources of gastric fluids and stomach acids that may be subject to reflux into a patient's mouth. The pH sensors (1225D, 1225F) placed along the proximal end of the oral insert device are likely, therefore, to be an early indicator of saliva having the highest acidity and lowest pH readings if gastro-esophageal reflux disease is an issue for the patient. Other sensors may be placed strategically as well, and practitioners have numerous options for designing sensor placement. All of the sensors are exposed to the patient's saliva for reading and recording pH values in a system as described herein.

In one embodiment, the sensors (1225) are connected to a computerized network at least partially housed within the mouth guard/oral insert (1218). The computerized network according to the disclosure set forth herein includes at least a power source (1210), such as a battery positioned in a portion of the oral insert and a transmitting component (1215) such as a transceiver that is powered by the power source to transmit the data to another component in the network. In one non-limiting embodiment, the transceiver (1215) is a wireless transceiver that transmits the gathered pH data along a wireless transmission network to a computer such as a server or even a local personal computer. The computer includes a processor and associated memory to calculate more detailed analyses for the pH data gathered over time.

The oral insert (1218) according to the disclosure herein is configured to use on patients that may not be able to express symptoms to a care giver or may be experiencing symptoms during sleep. Taking the sleep state as an example, in one embodiment, at least one section (1285) of the oral insert is adapted to direct saliva from the mouth across at least one sensor. In this regard, the oral insert may incorporate channels (1230) or at least contours in the construction of the device so that saliva is more likely to reach key sensor positions for analysis. Accordingly, the sensors may be positioned in wells that are slightly recessed to pool saliva onto the sensor. With this construction, the oral device may effectively measure pH of saliva in a patient's mouth when the patient's head is turned one way or another during sleep. Instead of saliva flowing along an inner side of a patient's cheeks and then swallowed, the channels (1230)

may direct the saliva to a sensor of interest. The channels (1230) described herein are not limited to any particular shape or configuration. The channels may be simple troughs, enclosed tunnels through the palate section (1220B), or simple inclines and contours that promote saliva delivery to the sensor.

The device of FIG. 12 is illustrated with data/electrical signal connectors (1255) that are suitable for data transmission to other computerized components in a system having components connected over a data transmission network. In the embodiment shown, the sensors (1225), a power source (1210), and a transceiver (1215) are the only components housed in the oral insert (1218) itself. This arrangement would therefore include capabilities to transmit data from the device in use in a patient's mouth to an outside computer receiver/transceiver for analysis by an associated processor implementing computer instructions of stored software designed for pH considerations. The embodiments of this disclosure, however, may include additional or fewer components of the system so long as the sensor data can be analyzed by a medical/dental professional, preferably in an automated and computerized setting. For example, as processing capabilities reside on more devices with smaller footprints, additional processing power may be implemented directly on or within the body of the oral insert (1218). Power options may also be varied and remain with the concepts disclosed herein.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, network device 102 may be applicable in other exchanges or routing protocols. Moreover, although network device 102 has been illustrated with reference to particular elements and operations that facilitate the communication process, these elements, and operations may be replaced by any suitable architecture or process that achieves the intended functionality of network device 102.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. Note also that an 'application' as used herein this Specification, can be inclusive of an executable file comprising instructions that can be understood and processed on a computer, and may further include library modules loaded during execution, object files, system files, hardware logic, software logic, or any other executable modules.

In example implementations, at least some portions of the activities may be implemented in software provisioned on networking device 102. In some embodiments, one or more of these features may be implemented in hardware, provided external to these elements, or consolidated in any appropriate manner to achieve the intended functionality. The various network elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

Furthermore, the network elements of FIG. 1 (e.g., network devices 102) described and shown herein (and/or their associated structures) may also include suitable interfaces for receiving, transmitting, and/or otherwise communicating data or information in a network environment. Additionally, some of the processors and memory elements associated with the various nodes may be removed, or otherwise consolidated such that single processor and a single memory element are responsible for certain activities. In a general sense, the arrangements depicted in the Figures may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc.

In some of example embodiments, one or more memory elements (e.g., memory 116) can store data used for the operations described herein. This includes the memory being able to store instructions (e.g., software, logic, code, etc.) in non-transitory media, such that the instructions are executed to carry out the activities described in this Specification. A processor can execute any type of instructions associated with the data to achieve the operations detailed herein in this Specification. In one example, processors (e.g., processor 114) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

These devices may further keep information in any suitable type of non-transitory storage medium (e.g., random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. Any of the memory items discussed herein should be construed as being encompassed within the broad term 'memory element.' Similarly, any of the potential processing elements, modules, and machines described in this Specification should be construed as being encompassed within the broad term 'processor.'

The list of network destinations can be mapped to physical network ports, virtual ports, or logical ports of the router, switches, or other network devices and, thus, the different sequences can be traversed from these physical network ports, virtual ports, or logical ports.

These and other embodiments supported by the disclosure herein are set forth in the claims that follow this detailed description.

The invention claimed is:

1. An apparatus for gathering pH data from a patient's mouth, comprising:
   an oral insert comprising a contoured region connected to a labial bow and a palate region connected to clasps for securing the oral insert;
   a plurality of flat pH sensors positioned in the palate region and the contoured region of the oral insert in respective positions configured to expose the flat pH sensors for measuring pH, wherein the respective positions correspond to respective biomarkers sensed in the respective positions;
   wherein the plurality of flat pH sensors are proximal pH sensors and distal pH sensors positioned on the oral insert in proximal and distal positions, and wherein the proximal positions are adjacent the clasps for securing the oral insert and distal positions are adjacent the labial bow;
   at least one data transmission device and at least one power device in respective positions in the palate region of the oral insert and separated from the distal pH sensors within the contoured region of the oral insert and further separated from proximal pH sensors within the palate region of the oral insert, wherein the separated data transmission device and separated power device are in electrical communication across the oral insert with all of the plurality of flat pH sensors and configured to transmit pH sensor data to a network;
   wherein proximal pH sensors provide respective pH sensor data corresponding to one respective biomarker related to gastroesophageal reflux disease (GERD) acid in the patient's saliva, and wherein the respective pH sensor data from the distal pH sensors corresponds to another respective biomarker for dietary acid exposures in the patient's mouth.

2. An apparatus according to claim 1, wherein said oral insert comprises a shape that fits against a roof of the patient's mouth.

3. An apparatus according to claim 1, wherein said oral insert comprises a Hawley retainer.

4. An apparatus according to claim 1, wherein said clasps comprise Adams clasps.

5. An apparatus according to claim 1, further comprising a receiver connected to a computer to retain the pH sensor data in computerized memory for analysis.

6. An apparatus according to claim 1, wherein said palate region and said contoured region are separable.

7. An apparatus according to claim 1, wherein said oral insert is removable from the mouth via manual manipulation.

8. An apparatus according to claim 1, wherein the flat pH sensors are so dimensioned as to fit within the patient's mouth.

9. The apparatus according to claim 1, further comprising mechanical fasteners attaching the pH sensors to the oral insert.

10. The apparatus according to claim 9, wherein the mechanical fasteners attach the pH sensors to the oral insert in a modular arrangement.

11. A system for recording pH levels in a patient's mouth for a period of time and diagnosing medical conditions, the system comprising:
   a processor in data communication with computerized memory storing computer implemented software configured with instructions to record pH readings of saliva in the patient's mouth;
   an oral insert comprising clasps and a labial bow, each for securing the oral insert in the patient's mouth;
   a plurality of pH sensors positioned on the oral insert in respective positions configured to expose the pH sensor to the saliva at a plurality of locations in the patient's mouth;
   wherein the plurality of pH sensors are proximal pH sensors and distal pH sensors positioned on the oral insert in proximal and distal positions, and wherein the proximal positions are adjacent the clasps for securing the oral insert and distal positions are adjacent the labial bow;
   at least one data transmission device and at least one power device positioned in the oral insert and separated from the pH sensors, wherein the separated data transmission device and separated power device are in electrical communication across the oral insert, via respectively separate circuits, with all of the plurality of flat pH sensors, and wherein the data transmission device is configured to transmit pH sensor data to a network;
   photographs documenting erosive lesions on certain teeth of the patient, said photographs being accessible for visual comparison to a scale showing a severity of dental erosion, wherein the comparison to the scale and the pH sensor data correlate acid exposure on the certain teeth; and
   suggested treatment data stored in the computerized memory and corresponding to levels of the severity of dental erosion on the scale.

12. The system according to claim 11, wherein the network is a wireless data communications network.

13. The system according to claim 11, wherein the oral insert comprises channels directing saliva from the patient's mouth to the pH sensor for determining the pH level.

14. The system according to claim 11, wherein the scale is a Keels-Coffield Severity Scale.

15. The system according to claim 11, wherein the comparison differentiates GERD acid exposures from dietary acid exposures in the mouth.

* * * * *